United States Patent [19]

Parikh et al.

[11] Patent Number: 5,660,858
[45] Date of Patent: Aug. 26, 1997

[54] CYCLOSPORIN EMULSIONS

[75] Inventors: Indu Parikh, Chapel Hill; Awadhesh Mishra, Durham, both of N.C.

[73] Assignee: Research Triangle Pharmaceuticals, Durham, N.C.

[21] Appl. No.: 627,187

[22] Filed: Apr. 3, 1996

[51] Int. Cl.$^6$ ............................ A61K 9/107; A61K 35/13
[52] U.S. Cl. ............................ 424/450; 514/143; 514/938
[58] Field of Search .................................. 424/450

[56] References Cited

U.S. PATENT DOCUMENTS

| 4,990,337 | 2/1991 | Kurihara et al. | 427/427 |
| 5,342,625 | 8/1994 | Hauer et al. | 424/455 |
| 5,527,537 | 6/1996 | Dietl | 424/45 |
| 5,529,785 | 6/1996 | Dietl | 424/450 |

FOREIGN PATENT DOCUMENTS 0 036 277  9/1981  European Pat. Off. .......... A61K 9/50

*Primary Examiner*—Thurman K. Page
*Assistant Examiner*—Murthy Sikha
*Attorney, Agent, or Firm*—Nixon & Vanderhye

[57] ABSTRACT

This invention comprises pharmaceutical compositions consisting essentially of an oil-in-water emulsion containing a synthetic medium chain triglyceride in which is dissolved a therapeutically effective amount of a cyclosporin, phospholipid and optionally free fatty acid or a salt thereof, non-ionic surfactant, ionic surfactant, glycerol, salts, buffers, preservative, osmotic modifier and antioxidant.

26 Claims, No Drawings

CYCLOSPORIN EMULSIONS

This invention relates to pharmaceutical compositions containing a cyclosporin in an oil-in-water emulsion and in particular features the use of medium chain length triglycerides and free fatty acids to enhance the solubility of the cyclosporin in the oil phase to form stable and heat sterilizable oil-in-water emulsions without the need of potential toxic additives for the lipophilic carrier.

BACKGROUND OF INVENTION

Cyclosporins, a group of nonpolar cyclic oligopeptides with immunosuppressant activity, are known to be very poorly soluble in water and are thus difficult to formulate into injectable preparations containing an acceptable quantity of the drug. Due to their poor solubility, cyclosporins have been formulated in various non-aqueous materials including organic solvents such as ethanol and polyoxyethylated castor oils [cremophors] which are potentially toxic.

The patent literature describes various formulations and pharmaceutical presentations of lipophilic drugs. U.S. Pat. No. 4,073,943 to Wretlind describes a carrier system for use in enhancing parenteral administration of a pharmacologically active oil-soluble agent, the carrier system being a stable, oil-in-water emulsion containing a pharmacologically inert lipoid as a hydrophobic phase dispersed in a hydrophilic buffer. The lipoid is dispersed in the emulsion as finely divided particles having a mean diameter of less than 1 micron. The active agent is oil-soluble and is predominantly dissolved in the lipoid. The compositions contain a lipophilic core of a fat of vegetable origin.

In the carrier system described the drug must be soluble in the lipoid, although it may have some solubility in the hydrophilic phase. The composition will usually consist of an inert oil or fat dispersed in an aqueous solution. To obtain a stable emulsion, it is necessary to include a stabilizer of natural or synthetic origin, for example phosphatides, polypropylene glycol, polyethylene glycol or polyglycerol monooleate.

U.S. Pat. No. 4,298,594 to Sears describes the controlled release of an active agent contained in a vehicle in the form of microreservoirs in non-vesicular form having diameters between 250 Å and 1000 Å, or vesicular form having diameters ranging between about 190 Å and about 300 Å, or both nonvesicular and vesicular forms. The vehicle is formed of a phospholipid constituent and a phospholipid-immiscible lipid constituent. Preferred phospholipid-immiscible lipids include triglyceride and/or cholesterol ester; the phospholipid-immiscible lipid must essentially be immiscible in the phospholipid bilayer. The nonvesicular form is a fat emulsion and the vesicular form is a liposome.

Cyclosporin-containing pharmaceutical formulations for intravenous administration are described in EPO 0 570829 A1 to Dietl. The emulsions are composed of cyclosporin microcrystals in an oily carrier composed of medium-chain triglyceride oil, together optionally with vegetable oil, phospholipid, non-ionic surfactant and ionic surfactant. The lipophilic core composition is composed of natural oil, optionally with free or sodium or potassium salt of a fatty acid.

In the present invention, the lipophilic core composition includes synthetic or derivatized triglycerides and optionally free fatty acids or salts thereof, which are capable of solubilizing more cyclosporin than natural oils and allow the preparation of emulsions with greater cyclosporin payloads. In the present invention, the cyclosporin is completely dissolved in the lipophilic core.

U.S. Pat. No. 4,725,442 to Haynes describes microdroplets from about 100 Angstroms to one micron in diameter having a sphere of a substantially water-insoluble drug dissolved in an organic liquid such as an alkane, a dialkyl ester, a long-chain ester, a hydrophobic ester, a biocompatible silicone, a biocompatible high molecular weight fluorocarbon, oil-soluble vitamin, the liquid and drug surrounded in a layer of phospholipid.

U.S. Pat. No. 5,342,625 to Hauer describes cyclosporin-containing pharmaceutical compositions in the form of a microemulsion preconcentrate having a hydrophilic phase component of a pharmaceutically acceptable di-or partial-ether or 1,2-propylene glycol; a lipophilic phase component, for instance an organic solvent such as ethanol, and a surfactant; when diluted 1:1 with water an oil-in-water microemulsion having average particle size of less than about 1,000Å is formed. Theses microemulsions do not contain a triglyceride core and are distinctly different from emulsions since they form spontaneously (do not require addition of energy).

U.S. Pat. No. 4,990,337 to Kurihara et al describes emulsions containing cyclosporin and a mixture of medium chain mono- or di-glycerides. The use of medium chain triglycerides and mono- and di-glycerides to solubilize cyclosporin A is discussed. Kurihara concludes that the use of triglycerides, even medium chain triglycerides, is not acceptable due to poor solubility of cyclosporine. The patentees report that cyclosporins have excellent solubility in the mono- and di-glycerides of intermediate molecular weight fatty acids, which are easily emulsified in water, and which can thus substantially improve the dispersibility of cyclosporin in water and aqueous media. However, it is generally known that mono- and di-glycerides have detergent properties which enhance irritation and damage to tissues.

It is an object of this invention to provide a pharmaceutically acceptable cyclosporin preparation with a high drug payload.

It is a further object of this invention to provide a pharmaceutically acceptable cyclosporin preparation without potentially toxic organic solvents such as ethanol and cremophors.

It is another object of this invention to provide a pharmaceutically acceptable cyclosporin preparation which can be used parenterally.

It is an additional object of this invention to provide a pharmaceutically acceptable cyclosporin preparation which can be heat sterilized.

It is a further object of this invention to provide a method of forming such a preparation.

SUMMARY OF THE INVENTION

This invention comprises pharmaceutical compositions consisting essentially of an oil-in-water emulsion containing a synthetic medium chain triglyceride in which is dissolved a therapeutically effective amount of a cyclosporin, phospholipid and optionally free fatty acid or a salt thereof, non-ionic surfactant, ionic surfactant, glycerol, salts, buffers, preservative, osmotic modifier and antioxidant.

The invention provides stable emulsions consisting of non-toxic excipients, which allow for delivery of high concentrations of cyclosporin (up to ~7.5% w/w cyclosporin A). We have found that medium chain triglycerides, as herein defined, have the ability to solubilize cyclosporin (~150–200 mg cyclosporin A/mL oil) and form stable emulsions without the need of potentially toxic additives such as ethanol, propylene glycol, cremophors and the like. Using lipids as stabilizers, the inventive emulsions of the present invention retain size stability during heat sterilization, storage, and under the stress conditions of shaking, vibrating and thermal cycling between 4 and 40° C.

Further entailed in this inventions is the addition of a free fatty acid or salt thereof to the medium chain triglycerides to further enhance the cyclosporin solubility (~300–450 mg cyclosporin A/mL oil).

Particularly preferred pharmaceutical compositions are essentially oil-in-water emulsions composed of about 10% to about 40% of a synthetic medium chain triglyceride containing $C_8$–$C_{12}$ fatty acid chains, about 1% to about 10% w/w of a cyclosporin dissolved in the triglyceride; about 1 to about 5% w/w of a natural or synthetic phospholipid, about 0.1 to about 10% w/w unsaturated free fatty acids or salts thereof to enhance the solubility of the cyclosporin; with the balance an aqueous phase optionally also including glycerol, salts, buffers, surfactants, antioxidants or preservatives.

Preferably the synthetic medium chain triglyceride has $C_8$–$C_{10}$ fatty acid chains, particularly the synthetic medium chain triglyceride contains $C_8$ fatty acid chains.

The invention also includes a method of preparing a stable emulsion of cyclosporin including the steps of: dissolving cyclosporin in a synthetic medium chain triglyceride to which has been added a cyclosporin solubility enhancing amount of an unsaturated free fatty acid or a salt thereof and phospholipid, to produce an oil phase; preparing an aqueous phase containing water, glycerol and also optionally an ionic or non-ionic surfactant; mixing the oil phase with the aqueous phase and subjecting the mixture to homogenizing conditions to prepare a stable cyclosporin emulsion in which substantially all of the particles have a size less than 1 µm; and heat sterilizing the emulsion.

DETAILED DESCRIPTION OF THE INVENTION

The cyclosporins are a class of pharmacologically active substances known primarily for their immunosuppressant activity primarily in organ transplants. Cyclosporin A, isolated as an amorphous powder from fungal sources by chromotography, is the most common form, however cyclosporins B through I have been identified and various synthetic analogues have been prepared. Preferred are cyclosporins A, B, D and G (*The Merck Index*, 11th Edition, 2759). The formulations of the present invention may contain about 0.1 to about 10% w/w, preferably at least 1%, and ideally between about 2.5 and about 7.5% cyclosporin.

The lipid component may be any natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted. The lipid component may also include cholesterol, sphingomyelin or combinations of any of the above-mentioned lipid components. The lipid component will normally represent between about 1 to about 10% w/w, preferably between about 1 to about 5% w/w.

The aqueous phase is primarily water plus glycerol, salts, buffers, osmotic modifiers, and the like. Nonionic or ionic surfactants, antioxidants and preservatives may be present.

The synthetic medium chain triglycerides employed in the compositions of the invention are characterized as having $C_8$–$C_{12}$ fatty acid chains, preferably $C_8$–$C_{10}$ fatty acid chains desirably predominantly $C_8$ fatty acid chain, or other derivatized (synthetic) triglycerides such as MIGLYOL 810, MIGLYOL 818 and MIGLYOL 812 (Hüls, Piscataway, N.J.) or LABRAFIL M 1944cs (Gatteffossé, Westwood, N.J.). The triglyceride may be a mixture of natural and synthetic triglycerides.

Also present may be unsaturated free fatty acids or salts of fatty acids such as linoleic acid (9,12 octadecadienoic acid) and linolenic acid (9,12,15 octadecatrienoic acid) in amounts preferably between 0.1 to about 10% and ideally between 1% to about 5%. The use of these acids, particularly linoleic acid or linolenic acid enhances the solubility of the cyclosporin in the medium chain triglyceride oil.

We have determined the solubility of cyclosporin A in a variety of natural oils and synthetic triglycerides. The results indicate that cyclosporin A is more soluble in medium chain triglycerides than long chain triglycerides.

| Natural oil or Synthetic Triglyceride | Solubility (room temp.) |
| --- | --- |
| Coconut Oil (Glycerides, predominantly C12 & C14) | 175 mg/mL |
| Olive Oil (Glycerides, predominantly C18 & C16) | 25 mg/mL |
| Peanut Oil (Glycerides, predominantly C18) | 40 mg/mL |
| Safflower Oil (Glycerides, predominantly C18) | 70–80 mg/mL |
| Soybean Oil (Glycerides, predominantly C18 & C16) | 36 mg/mL |
| Labrafac Lipophile (Triglycerides, mixed C8 & C10) | 150 mg/mL |
| Miglyoyl 810 (Triglycerides, mixed C8 & C10) | 150 mg/mL |
| Miglyol 812 (Triglycerides, mixed C8 & C12) | 125 mg/mL |
| Miglyoyl 818 (Triglycerides, mixed C8 & C18) | 200 mg/mL |

The use of synthetic triglycerides, in contrast to the natural oil, greatly increases the payload of cyclosporin. In addition, synthetic sources of triglycerides are chemically homogeneous, contain fewer and known impurities, and have less batch to batch variation.

We have found that the solubility of cyclosporin is further enhanced by the addition of free fatty acids, such as linoleic and linolenic acid, to the triglycerides. Many commercially available parenteral emulsions are prepared at or near pH 9 to increase the stability of the emulsion. In contrast to conventional practice, we have found that enhanced cyclosporin solubility in emulsions containing unsaturated free fatty acids such as linoleic acid or linolenic acid is achieved at pHs in the range of about 4.0 to about 7.0. Addition of free fatty acid also improves the stability of the emulsion.

In addition, the physical stability of the emulsion may be enhanced by the addition of a non-ionic surfactant or ionic surfactant. These non-ionic surfactants are pharmaceutically acceptable and do not include solvents such as ethanol or cremophors, which are potentially toxic.

The following table reports the solubility of cyclosporin, in mg/mL at room temperature, in a variety of commercially available synthetic oils and mixed lipids:

| Oil | Solubility (room temp) |
| --- | --- |
| Labrofac Lipophile | 150 mg/mL |
| Miglyol 810 | 150 mg/mL |
| Miglyol 812 | 125 mg/mL |
| Miglyol 818 | 200 mg/mL |

-continued

| Oil | Solubility (room temp) |
|---|---|
| Miglyol 810/linoleic acid | |
| 90:10 w/w | 335 mg/mL |
| 66:33 w/w | 400 mg/mL |
| Miglyol 818/linoleic acid | |
| 90:10 w/w | 425 mg/mL |
| 66:33 w/w | 430 mg/mL |
| Linoleic acid | >575 mg/mL |

While the solubility of cyclosporin in linoleic acid is extremely high, it is too acidic to be used alone in an emulsion formulation. When used in combination with a synthetic medium chain triglyceride it enhances the solubility of the cyclosporin in the oil phase.

Miglyol neutral oils [Hüls, Piscataway, N.J.] are esters of medium chain fatty acids. To obtain the medium chain C8–C10 fatty acids, coconut oil is hydrolyzed and the resulting fatty acid mixture is fractionated. The fatty acid mixtures are then esterified with glycerol or other polyhydric alcohols. Thus, Miglyols are synthetic (sometimes referred to as non-natural) and not natural triglycerides.

| Miglyol Oil | C8 (caprylic) | C10 (capric) |
|---|---|---|
| Miglyol 810 | 70–80% | 20–30% |
| Miglyol 812 | 50–65% | 30–45% |
| Miglyol 818 | 40–60% | 25–40% |

Labrofac Lipophile WL1349 [Gattefossé Westwood, N.J.] is a synthetic mixture of medium chain triglycerides (mostly C8 and C10) isolated from coconut oil.

The emulsions of the present invention are prepared as follows: An appropriate amount of cyclosporin is dissolved in the desired oil or mixture of oils at the desired temperature. Also added to this mixture and dispersed are phospholipids. This oil solution is added to an aqueous solution of glycerol, with or without a non-ionic or ionic surfactant, with or without an antioxidant and with or without a preservative. The resulting mixture is then adjusted to the desired pH and homogenized at the desired pressure in batch-wise or continuous cycles until the desired particle size is obtained, typically less than 500 nm volume weighted mean particle size. Several homogenizers are available including Rannie homogenizers (APV) and microfluidizers (Microfluidics Systems). The resulting emulsion can be further pH adjusted and filter- or heat-sterilized.

EXAMPLE 1

A cyclosporin A fatty acid emulsion formulation having the following components

| Components | % w/w |
|---|---|
| Cyclosporin A | 5% |
| Egg Phospholipid | 2.25% |
| Dimyristoyl phosphatidylglycerol (DMPG) | 0.25% |
| Miglyol 810 | 15% |
| Linoleic acid | 5% |
| Glycerol | 5% |
| Water, to make | 100 g |
| pH | 5.5 | was prepared by homogenization. The oil phase was prepared by dispersing is cyclosporin A in the triglyceride (Miglyol 810) and linoleic acid mixture. Egg phospholipid and dimyristoylphosphatidylglycerol (DMPG) were added to this mixture and dispersed in the oil phase and heated to 60°–70° C. until the components were dissolved. The oil phase was added to the aqueous phase containing glycerol and mixed well; the resulting mixture had an initial pH of about 3–4. Sodium hydroxide, aqueous solution, was added to provide a final pH of 5.5. The mixture was then homogenized and heat sterilized. The particle size ranges of a representative resulting emulsion were as follows.

| Particle Size Ranges: (Measurement error ~ 5–10%) | |
|---|---|
| Minimum size | 20 nm |
| 25% below | 175–200 nm |
| 50% below | 225–300 nm |
| 75% below | 300–375 nm |
| 99% below | 600–700 nm |
| a few tenths of a % | 1–2 μm |

EXAMPLE 2

In the manner of Example 1, a cyclosporin-containing emulsion with increased levels of linoleic acid and Miglyoyl, to compensate for the higher pH, was prepared having the following components:

| Components | % w/w |
|---|---|
| Cyclosporin A | 7.5% |
| Egg phospholipid | 1.5% |
| Miglyol 810 | 22.5% |
| Linoleic acid | 7.5% |
| Glycerol | 2.5% |
| Water, to make | 100 g |
| pH | 8:80 |
| Particle Size After Heat Sterilization (mean ± std dev.) | 81 ± 39 nm. |

EXAMPLE 3

In the manner of Example 1, a cyclosporin-containing emulsion was prepared without free fatty acid having the following components:

| Components | % w/w |
|---|---|
| Cyclosporin A | 2% |
| Egg phospholipid | 2.5% |
| Miglyol 818 | 15% |
| Glycerol | 2.5% |
| Water, to make | 100 g |
| pH | 7.0 |
| Particle Size After Heat Sterilization (mean ± std dev.) | 103 ± 34 nm |

EXAMPLE 4

In the manner of Example 1, a cyclosporin-containing emulsion with a non-ionic surfactant and without a free fatty acid was prepared having the following components:

| Components | % w/w |
| --- | --- |
| Cyclosporin A | 3% |
| Egg phospholipid | 2.0% |
| Miglyol 810 | 20% |
| Tween 20 | 1% |
| Glycerol | 5.0% |
| Water, to make | 100 g |
| pH | 6.5 |
| Particle Size (mean ± std dev.) | 129 ± 27 nm |

EXAMPLE 5

In the manner of Example 1, a cyclosporin-containing emulsion with a non-ionic detergent was prepared having the following components:

| Components | % w/w |
| --- | --- |
| Cyclosporin A | 5% |
| Egg phospholipid | 1.0% |
| DMPG | 0.2% |
| Miglyol 810 | 15% |
| Linoleic acid | 5% |
| Glycerol | 2.5% |
| Tween 20 | 0.5% |
| Water, to make | 100 g |
| pH | 5.6 |
| Particle Size After Heat Sterilization (mean ± std dev.) | 318 ± 105 nm |

EXAMPLE 6

In the manner of Example 1, a cyclosporin-containing emulsion with natural and synthetic triglycerides were prepared having the following components:

| Components | % w/w |
| --- | --- |
| Cyclosporin A | 5% |
| Egg phospholipid | 2% |
| Miglyol 810 | 23.75% |
| Glycerol | 3.75% |
| Water, to make | 100 g |
| pH | 7.0 |
| Particle Size (mean ± std dev.) | 294 ± 76 nm |

What is claimed is:

1. A pharmaceutical composition consisting essentially of an oil-in-water emulsion composed of a synthetic medium chain triglyceride containing primarily $C_8$–$C_{12}$ fatty acid chains in which is dissolved a therapeutically effective amount of cyclosporin, phospholipid and an aqueous phase.

2. A pharmaceutical composition consisting essentially of an oil-in-water emulsion composed of a synthetic medium chain triglyceride containing primarily $C_8$–$C_{12}$ fatty acid chains in which is dissolved a therapeutically effective amount of cyclosporin, phospholipid, a free fatty acid or a salt thereof and an aqueous phase.

3. A pharmaceutical composition consisting essentially of an oil-in-water emulsion composed of about 10% to about 40% of a synthetic medium chain triglyceride containing $C_8$–$C_{12}$ fatty acid chains;

about 1% to about 10% w/w of cyclosporin;

about 1 to about 5% w/w of natural and/or synthetic phospholipid;

about 0.1 to about 10% w/w unsaturated free fatty acids or salts thereof; and balance aqueous phase optionally also including glycerol, salts, buffers, surfactants, antioxidants, osmotic modifiers or preservatives.

4. A pharmaceutical composition consisting essentially of an oil-in-water emulsion composed of about 10% to about 40% of a synthetic medium chain triglyceride containing $C_8$–$C_{12}$ fatty acid chains;

about 1% to about 10% w/w of cyclosporin;

about 1 to about 5% w/w of natural or synthetic phospholipid; and balance aqueous phase optionally also including glycerol, salts, buffers, surfactants, antioxidants, osmotic modifiers or preservatives.

5. The composition of claims 1, 2, 3 or 4 wherein the synthetic medium chain triglyceride has $C_8$–$C_{10}$ fatty acid chains.

6. The composition of claim 5 wherein the synthetic medium chain triglyceride consists primarily of $C_8$ fatty acid chains.

7. The composition of claims 1, 2, 3 or 4 wherein the phospholipid is selected from the group consisting of phosphatidylcholine, phosphatidylethanolamine, phosphatidylserine, phosphatidylinositol, phosphatidylglycerol, phosphatidic acid, lysophospholipids, egg phospholipid, soy phospholipid or a mixture thereof.

8. The composition of claim 2 or 3 wherein the unsaturated free fatty acid is linoleic acid, linolenic acid or a mixture thereof.

9. The composition of claim 2, 3 or 4 wherein the composition contains from about 2.5 to about 7.5% w/w cyclosporin.

10. The composition of claim 1, 2, 3 or 4 wherein the cyclosporin is cyclosporin A.

11. The composition of claim 3 or 4 wherein the amount of phospholipid is up to about 3% w/w.

12. The composition of claim 2 or 3 wherein the amount of free fatty acid is about 1% to about 5% w/w.

13. The composition of claim 1, 2, 3 or 4 wherein the aqueous phase contains water and at least one of an antioxidant, preservative, osmotic modifier, salt, glycerol, ionic surfactant or non-ionic surfactant.

14. The composition of claim 1, 2 or 3 wherein the emulsion additionally contains natural triglycerides.

15. A method of preparing a stable emulsion of cyclosporin comprising the steps of:

(1) dissolving cyclosporin in a synthetic medium chain triglyceride to which has been added a cyclosporin solubility enhancing amount of an unsaturated free fatty acid or a salt thereof and phospholipid to produce an oil phase;

(2) preparing an aqueous phase containing water and optionally an antioxidant, preservative, osmotic modifier, salt, glycerol, ionic surfactant or non-ionic surfactant;

(3) mixing the oil phase with the aqueous phase and subjecting the mixture to homogenizing conditions to prepare a stable cyclosporin emulsion in which substantially all of the particles have a size less than 1 μm.

16. The process of claim 15 including the additional step (4) of:

heat or filter sterilizing the stable emulsion of step (3).

17. The process of claim 15 wherein the synthetic medium chain triglyceride has $C_8$–$C_{10}$ fatty acid chains.

18. The process of claim 16 wherein the synthetic medium chain triglyceride consists primarily of $C_8$ fatty acid chains.

19. The process of claim 15 wherein the phospholipid is selected from the group consisting of phosphatidylcholine, phosphatidylethanolamine, phosphatidylserine, phosphatidylinositol, phosphatidylglycerol, phosphatidic acid, lysophospholipids, egg phospholipid, soy phospholipid and phosphatidyl glycerol.

20. The process of claim 15 wherein the unsaturated free fatty acid is linoleic acid, linolenic acid or a mixture thereof.

21. The process of claim 15 wherein the emulsion contains about 2.5 to about 7.5% w/w cyclosporin.

22. The process of claim 15 wherein the cyclosporin is cyclosporin A.

23. The process of claim 15 wherein the amount of phospholipid is up to about 3% w/w.

24. The process of claim 15 wherein the amount of free fatty acid or fatty acid salt is about 1% to about 5% by w/w.

25. The process of claim 15 wherein the aqueous phase contains water and optionally an antioxidant, preservative, osmotic modifier, salt, glycerol, ionic surfactant or non-ionic surfactant.

26. The process of claims 15 wherein the cyclosporine is dissolved in a mixture of synthetic and natural triglycerides.

* * * * *